United States Patent
Lee et al.

(10) Patent No.: US 8,848,051 B2
(45) Date of Patent: Sep. 30, 2014

(54) METHOD OF SCANNING BIOCHIP AND APPARATUS FOR PERFORMING THE SAME

(75) Inventors: Kyu-sang Lee, Suwon-si (KR); Carl S. Brown, Seattle, WA (US); Kyla Teplitz, Seattle, WA (US); Steve Goodson, Seattle, WA (US)

(73) Assignees: Samsung Electronics, Co., Ltd., Suwon-Si (KR); Applied Precision, Inc., Issaquah, WA (US)

( * ) Notice: Subject to any disclaimer, the term of this patent is extended or adjusted under 35 U.S.C. 154(b) by 601 days.

(21) Appl. No.: 12/703,843

(22) Filed: Feb. 11, 2010

(65) Prior Publication Data

US 2010/0208061 A1    Aug. 19, 2010

(30) Foreign Application Priority Data

Feb. 11, 2009    (KR) .................. 10-2009-0011209

(51) Int. Cl.
*G01N 21/55* (2014.01)
*G01N 21/64* (2006.01)
*G06T 7/00* (2006.01)

(52) U.S. Cl.
CPC ........ *G01N 21/6452* (2013.01); *G01N 21/6486* (2013.01); *G06T 7/0046* (2013.01); *G06T 2207/30024* (2013.01); *G06T 2207/10056* (2013.01); *G01N 21/6456* (2013.01); *G06T 2207/30204* (2013.01)
USPC .......................................... 348/135; 356/445

(58) Field of Classification Search
CPC .......... G01N 21/6452; G01N 21/6456; G01N 21/6486; G06T 7/0046; G06T 2207/10056; G06T 2207/30024; G06T 2207/30204
USPC ............................... 348/94, 135, 87; 356/445
See application file for complete search history.

(56) References Cited

U.S. PATENT DOCUMENTS 6,160,908 A * 12/2000 Hakozaki ...................... 382/154
6,259,473 B1 * 7/2001 Iko et al. .......................... 348/80
(Continued)

FOREIGN PATENT DOCUMENTS

CN    101013136 A    8/2007
CN    101203744 A    6/2008
(Continued)

OTHER PUBLICATIONS

Peter J. Shaw, et al, "Tilted view reconstruction in optical microscopy: Three-dimensional reconstruction of *Drosophila melanogaster* embryo nuclei", Jan. 1989, Biophys. J. V. 55, p. 101.*

(Continued)

*Primary Examiner* — Richard Torrente
*Assistant Examiner* — Frank Huang
(74) *Attorney, Agent, or Firm* — Leydig, Voit & Mayer, Ltd.

(57) ABSTRACT

An apparatus for scanning a biometric device includes a camera that scans the biometric device to generate images, and a computer that extracts data from the images. The computer measures three-dimensional locations of at least three different positions on a surface of the biometric device, determines a virtual approximation plane or a curved surface with respect to the surface of the biometric device based on the measured three-dimensional locations, determines imaging locations of two or more panels disposed on the biometric device based on the virtual approximation plane or the curved surface, obtains individual images of the two or more panels by scanning the biometric device based on the determined imaging locations, and extracts overall data of the biometric device from the individual images of the two or more panels.

21 Claims, 5 Drawing Sheets

(56) References Cited

U.S. PATENT DOCUMENTS

| | | | |
|---|---|---|---|
| 6,556,783 B1 * | 4/2003 | Gelphman | 396/20 |
| 6,773,935 B2 * | 8/2004 | Watkins et al. | 438/14 |
| 6,917,696 B2 * | 7/2005 | Soenksen | 382/128 |
| 7,209,236 B2 | 4/2007 | Tanaami et al. | |
| 7,262,858 B2 * | 8/2007 | Lin et al. | 356/445 |
| 2004/0233461 A1 * | 11/2004 | Armstrong et al. | 356/620 |
| 2005/0078861 A1 * | 4/2005 | Usikov | 382/131 |
| 2007/0031993 A1 * | 2/2007 | Nemets et al. | 438/110 |
| 2009/0295963 A1 * | 12/2009 | Bamford et al. | 348/302 |

FOREIGN PATENT DOCUMENTS

| | | |
|---|---|---|
| JP | 2004-333333 | 11/2004 |
| JP | 2006-337245 | 12/2006 |
| KR | 10-2006-0104089 | 10/2006 |
| WO | WO 2006/128321 A1 | 12/2006 |

OTHER PUBLICATIONS

Chinese Intellectual Property Office, Office Action in Chinese Patent Application No. 201010121422.6, Jul. 18, 2013, 11 pp.

* cited by examiner

METHOD OF SCANNING BIOCHIP AND APPARATUS FOR PERFORMING THE SAME

CROSS-REFERENCE TO RELATED APPLICATION

This application claims priority to Korean Patent Application No. 10-2009-0011209, filed on Feb. 11, 2009, and all the benefits accruing therefrom under 35 U.S.C. §119, the content of which in its entirety is herein incorporated by reference.

BACKGROUND

1) Field

The general inventive concept relates to a method of scanning a biochip, and more particularly, to a method of scanning a biochip at a substantially improved speed.

2) Description of the Related Art

A biochip is a biometric device typically made by combining biogenic organic materials, such as enzymes, proteins, antibodies and deoxyribonucleic acid ("DNA") of living creatures, microorganisms, and cells, organs and nerves of animals and plants, for example, into a microchip, which is similar to a semiconductor chip. More particularly, a DNA biochip, for example, is a device for detecting DNA, and is made by arranging several hundred to several hundred thousand types of DNA, which have different base sequences, and of which functions in cells are clarified, in a single spiral shape (instead of a double spiral shape) within a small space on a substrate, which may be a glass substrate or a semiconductor substrate, for example. Generally, a collection of single spiral shaped DNA having the same base sequence is referred to as a spot, and approximately twenty to thirty bases are typically connected to form a single spot. Similarly, in a protein biochip, a collection of antibodies or receptors, which may be combined with the same protein, is referred to as a spot.

When a sample is dropped onto a biochip, only a gene or a protein corresponding to a certain spot is combined with the spot, and genes or proteins which are not combined with spots on the biochip are washed away. Thus, genetic information of the sample is easily obtained by identifying spots on the biochip, which have combined with the sample. For example, aspects of unique genetic expressions or mutations in a certain cell or tissue are easily analyzed using the biochip. Also, the biochip may be used in massive analyses of genetic expressions, pathogenic bacteria infection tests, antibiotic-resistance tests, research on biological reactions with respect to environmental factors, food safety inspection, identification of criminals, development of new drugs and medical inspection of animals and plants, for example.

Various methods of identifying spots on a biochip, which are combined with genes of the sample dropped onto the biochip, have been suggested, and, specifically, a fluorescent detection method is one example. In the fluorescent detection method, a fluorescent material that emits light of a certain color when excited by excitation light is combined with the sample. The spots combined with the sample are identified by dropping the sample onto the biochip and then analyzing a fluorescent image obtained by projecting excitation light onto the biochip.

In general, a scanner device, which obtains the fluorescent image by projecting the excitation light onto a biochip, obtains the fluorescent image by scanning the biochip using a pixel size from about 5 micrometers (μm) to about 10 μm. A basic unit of scanning is referred as a panel, and a single biochip generally includes several hundred panels. In addition, several hundred to several hundred thousand spots form a microarray on a single panel. Generally, fluorescent images of individual panels are obtained by sequentially scanning the individual panels by moving the biochip and a camera of the scanner device. Thus, a single large biochip image is formed by connecting the individual fluorescent images of the panels. Accordingly, spots of the biochip, which are combined with the sample, are analyzed.

However, when a surface of a microarray of a biochip is tilted, a brightness and location of a fluorescent image is accurately obtained by focusing on each individual panel. However, this means that a high-density biochip, having a large number of panels, requires an excessive scanning time to focus on each panel. Also, when the microarray of the biochip is not accurately arranged, e.g., is not arranged in parallel with a moving axis of the camera of the scanner device, such as if the biochip is rotated, for example, portions of a fluorescent image are cut off and, thus, the entire fluorescent image cannot be scanned. Furthermore, it is tedious and inconvenient to rotate and connect fluorescent images of individual panels to form a single large biochip image, thereby substantially increasing a time required to analyze the sample.

SUMMARY

Provided is a method of rapidly and accurately scanning a biochip without changing the structure of a scanner device for obtaining a fluorescent image of the biochip. Provided also is an apparatus for performing the method.

To achieve the above and/or other aspects, provided is a method of scanning a biochip, the method including measuring three-dimensional locations of at least three different positions on a surface of the biochip, determining one of a virtual approximation plane and a curved surface with respect to the surface of the biochip based on the measured three-dimensional ("3D") locations, determining imaging locations of two or more panels disposed on the biochip based on the one of the virtual approximation plane and the curved surface, obtaining individual images of the two or more panels by scanning the biochip based on the determined imaging locations, and extracting overall data of the biochip from the individual images of the two or more panels.

The two or more panels may be adjacent to each other, and the at least three different positions may be target marks on a substrate of the biochip.

The target marks may be disposed outside a microarray of spots disposed on the substrate.

The method may further include focusing a camera on the target marks. The measured 3D locations of the target marks may be calculated based on a degree of motion of a stage on which the biochip is disposed.

The one of the virtual approximation plane and the curved surface may be determined by using a least squares method based on the measured 3D locations.

The determining the imaging locations may include determining a degree of rotation and a degree of tilt of the biochip based on the one of the virtual approximation plane and the curved surface, determining x and y coordinates of center portions of the two or more panels based on the determined degree of rotation of the biochip, determining z coordinates of the center portions of the two or more panels based on the determined degree of tilt of the biochip, and calculating three-dimensional coordinates of the imaging locations based on a focal length of a camera and the x, y and z coordinates of the center portions of the two or more panels.

The determining the x and y coordinates may include determining x and y coordinates of a center portion of an initially scanned panel of the two or more panels, and determining x and y coordinates of center portions of subsequently scanned panels of the two or more panels, based on widths and lengths of each of the two or more panels and the determined degree of rotation of the biochip.

The determining the z coordinates may include determining a z coordinate of a center portion of an initially scanned panel of the two or more panels; and determining z coordinates of center portions of subsequently scanned panels of the two or more panels, based on widths and lengths of each of the two or more panels and the determined degree of tilt of the biochip.

The obtaining the individual images of the panels comprises scanning the two or more panels by moving the camera based on the determined imaging locations.

The extracting the overall data of the biochip may include performing a gridding operation on an individual image of an individual panel of the two or more panels to coordinate locations of spots in the individual panel and to evaluate a brightness of each of the spots in the individual panel; performing the gridding operation on individual images of other panels of the two or more panels; and extracting data of the entire biochip based on results of the gridding operation performed on the individual images of each of the two or more panels.

The performing the gridding operation on the individual images of each of the two or more panels may include rotating the individual images by the degree of rotation of the biochip.

The performing the gridding operation on the individual images of each of the two or more panels may include compensating the brightnesses of the spots based on a tilt direction and the degree of tilt of the biochip.

The extracting the overall data of the biochip may include performing a gridding operation on an individual image of an individual panel of the two or more panels to coordinate locations of spots in the individual panel and to evaluate a brightness of each of the spots in the individual panel, performing the gridding operation on individual images of other panels of the two or more panels, and extracting data of the entire biochip based on results of the gridding operation performed on the individual images of each of the two or more panels.

The extracting the data of the entire biochip may include calculating relative coordinates of single panels of the two or more panel with respect to the other panels of the two or more panels, converting coordinates of the spots on each of the panels of the two or more panels into coordinates referenced to the entire biochip based on coordinates of each of the panels and the coordinates of the spots on each of the panels, and matching brightness data of the spots on each of the panels, which is calculated by performing the gridding operation, with the converted coordinates of the spots on each of the panels.

The converting the coordinates of the spots may include multiplying the coordinates of each of the panels by a number of spots arranged in X and Y directions on each of the panels, and adding a resultant value of the multiplying the coordinates to the coordinates of the spots on each of the panels.

The number of spots arranged in the X and Y directions on each the panels is determined based on a value stored in advance of the multiplying the coordinates of each of the panels by the number of spots or, alternatively, the number of spots arranged in the X and Y directions on each the panels may be calculated when the gridding operation is performed.

Panel marks may be formed on each of the two or more panels, and the panel marks may be formed at corners of each of the two or more panels.

Also provided is biochip scanning apparatus including a stage, a biochip disposed on the stage, a camera that scans the biochip to generate images, and a computer that controls the stage and the camera, and extracts data from the biochip by analyzing the images. The computer controls the stage and the camera to scan the biochip by: measuring three-dimensional locations of at least three different positions on a surface of the biochip; determining one of a virtual approximation plane and a curved surface with respect to the surface of the biochip based on the measured three-dimensional locations; determining imaging locations of two or more panels disposed on the biochip based on the one of the virtual approximation plane and the curved surface; obtaining individual images of the two or more panels by scanning the biochip based on the determined imaging locations; and extracting overall data of the biochip from the individual images of the two or more panels.

The at least three different positions may be target marks on a substrate of the biochip, the target marks are disposed outside a microarray of spots disposed on the substrate, and the extracting the overall data of the biochip may include performing a gridding operation on two or more individual images of each of the two or more panels to coordinate locations of the spots on each of the two or more panels and to evaluate a brightness of each of the spots.

Also provided is apparatus for scanning a biometric device. The apparatus includes a camera which scans the biometric device to generate images and a computer which extracts data from the images. The computer measures three-dimensional locations of at least three different positions on a surface of the biometric device, determines one of a virtual approximation plane and a curved surface with respect to the surface of the biometric device based on the measured three-dimensional locations, determines imaging locations of two or more panels disposed on the biometric device based on the one of the virtual approximation plane and the curved surface, obtains individual images of the two or more panels by scanning the biometric device based on the determined imaging locations, and extracts overall data of the biometric device from the individual images of the two or more panels.

The biometric device may be a deoxyribonucleic acid biochip or a protein biochip.

The at least three different positions may be target marks on a substrate of the biometric device, the target marks may be disposed outside a microarray of spots disposed on the substrate, and panel marks may be formed at corners of each of the two or more panels.

To achieve the above and/or other aspects, provided is a biochip scanning apparatus including a stage for mounting a biochip; a camera for scanning the biochip; and a computer for controlling the stage and the camera and extracting data by analyzing images obtained by the camera, wherein the computer controls the stage and the camera to scan the biochip based on the above-described method.

BRIEF DESCRIPTION OF THE DRAWINGS

The above and/or other aspects will become more readily apparent and more readily appreciated from the following description, taken in conjunction with the accompanying drawings, in which.

DETAILED DESCRIPTION

The invention now will be described more fully hereinafter with reference to the accompanying drawings, in which various example embodiments are shown. This invention may, however, be embodied in many different forms, and should not be construed as limited to the example embodiments set forth herein. Rather, these example embodiments are provided so that this disclosure will be thorough and complete, and will fully convey the scope of the invention to those skilled in the art. Like reference numerals refer to like elements throughout.

It will be understood that when an element is referred to as being "on" another element, it can be directly on the other element or intervening elements may be present therebetween. In contrast, when an element is referred to as being "directly on" another element, there are no intervening elements present. As used herein, the term "and/or" includes any and all combinations of one or more of the associated listed items.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of the present invention.

The terminology used herein is for the purpose of describing particular example embodiments only and is not intended to be limiting. As used herein, the singular forms "a," "an" and "the" are intended to include the plural forms as well, unless the context clearly indicates otherwise. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Furthermore, relative terms, such as "lower" or "bottom" and "upper" or "top," may be used herein to describe one element's relationship to another element as illustrated in the Figures. It will be understood that relative terms are intended to encompass different orientations of the device in addition to the orientation depicted in the Figures. For example, if the device in one of the figures is turned over, elements described as being on the "lower" side of other elements would then be oriented on "upper" sides of the other elements. The exemplary term "lower," can therefore, encompasses both an orientation of "lower" and "upper," depending on the particular orientation of the figure. Similarly, if the device in one of the figures is turned over, elements described as "below" or "beneath" other elements would then be oriented "above" the other elements. The exemplary terms "below" or "beneath" can, therefore, encompass both an orientation of above and below.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

Hereinafter, example embodiments of the general inventive concept will be described in further detail with reference to the accompanying drawings.

Figure 1:
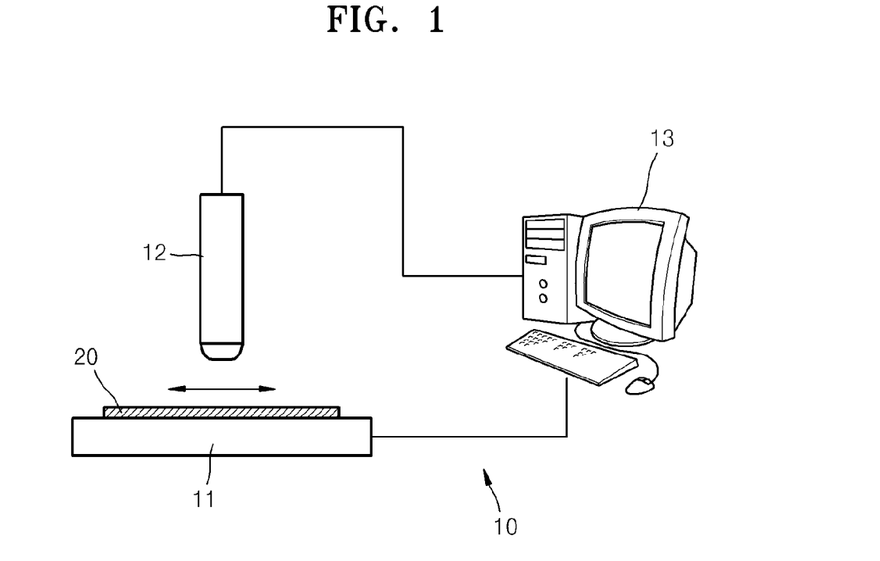
FIG. 1 is a perspective view of a scanner device for obtaining a fluorescent image by projecting light onto a biochip, according to an example embodiment.

FIG. 1 is a perspective view of an example embodiment a biochip scanner device 10 that obtains a fluorescent image by projecting light onto a biochip and extracts data by analyzing the fluorescent image. Referring to FIG. 1, the biochip scanner device 10 includes a stage 11 on which a biochip 20 (FIG. 2) is disposed, e.g., is mounted, a camera 12 that scans the biochip 20 and a computer 13 that controls the stage 11 and the camera 12 and extracts data by analyzing an image obtained by the camera 12. The stage 11 is referred to as an "XYZ stage" that moves the biochip 20 to be scanned in X, Y and Z directions of the camera 12 (described in further detail below with reference to FIG. 5). In alternative example embodiments, the biochip 20 may be fixed, and the camera 12 may be moved in the X, Y and Z directions by the stage 11. Hereinafter, for purposes of explanation, example embodiments will be described wherein the camera 12 moves, but it will be noted that, in additional example embodiments, the movement may actually be the movement of the biochip 20 mounted on the stage 11, or, more broadly, the movement in one or more embodiments may be any combination of movements that result in relative motion between the camera 12 and the biochip 20.

Figure 6:
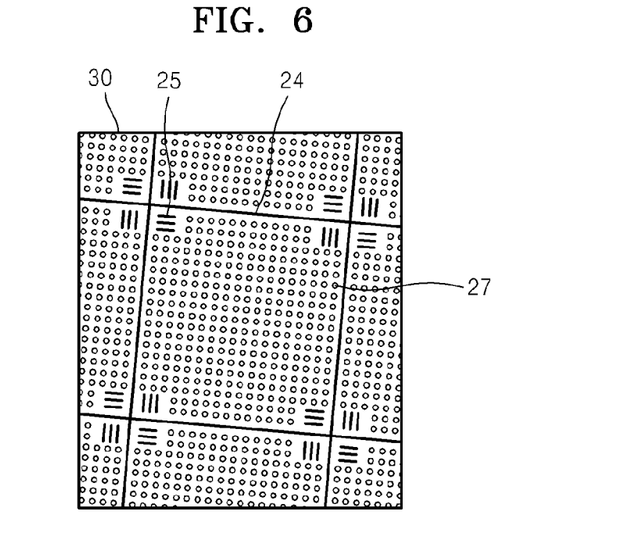
FIG. 6 is a plan view of an image of a single panel, which is obtained by a camera of a scanner device, according to an example embodiment.

In one or more embodiments, the camera 12 moves relative to the biochip 20, and obtains an image of a microarray 22 (FIG. 2) including spots 27 (FIG. 6) on panels 24 (FIG. 2) the biochip 20. Thus, as described above with respect to a conventional device, if the biochip 20 is rotated and/or tilted with respect to a moving axis (e.g., X-, Y- and/or Z-axes) of the camera 12, an accurate image cannot be obtained, and a substantially increased amount time/and or additional equipment is required to obtain an accurate image. In one or more example embodiments, however, the abovementioned deficiencies are overcome, and an accurate image is obtained at a high speed without requiring additional time or expensive optical equipment to the biochip scanner device 10 illustrated in FIG. 1, as will now be described in greater detail with reference to FIGS. 2-7.

Figure 7:
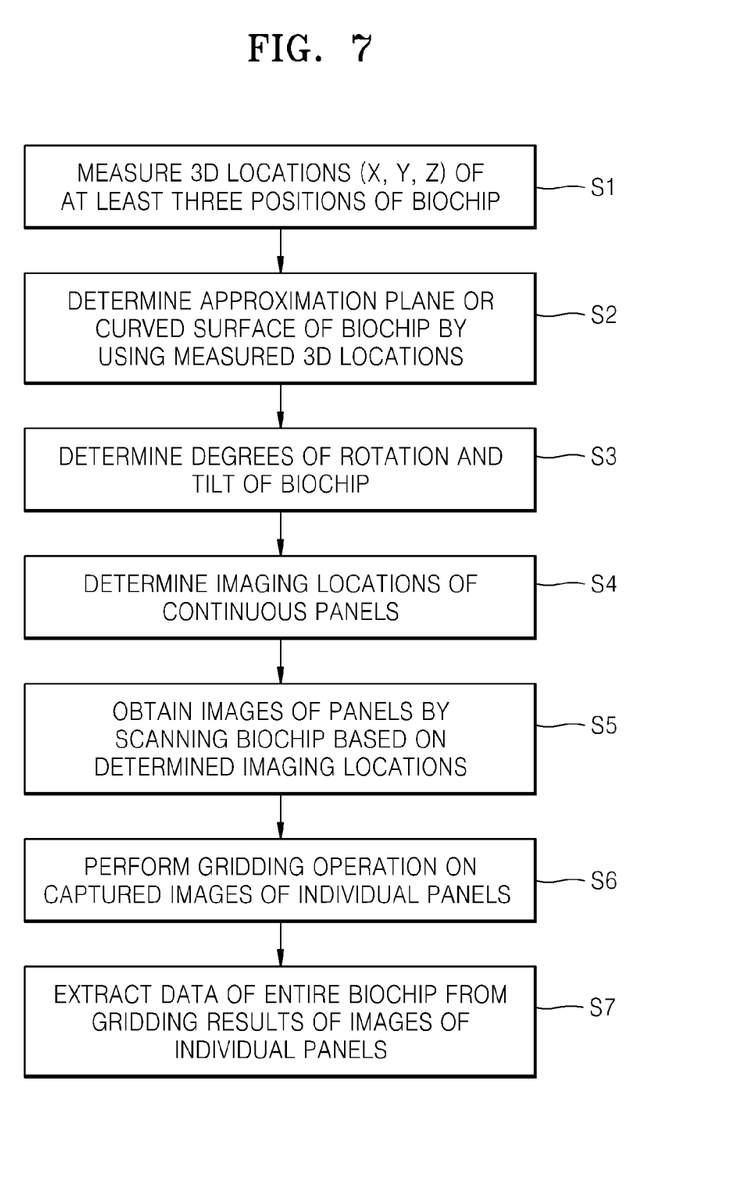
FIG. 7 is a flowchart of a method of scanning a biochip according to an example embodiment.

FIG. 7 is a flowchart of an example embodiment of a method of scanning the biochip 20, which obtains an accurate image at high speed without adding expensive optical equipment to the biochip scanner device 10 illustrated in FIG. 1.

Referring now to FIGS. 1 and 7, in operation 51, the camera 12 (FIG. 1) moves, under control of the computer 13, to a position above the biochip 20 mounted on the stage 11. The camera 12 moves in the X, Y and Z directions above the biochip 20 and measures three-dimensional ("3D") locations (e.g., locations with X, Y, Z coordinates) of, for example, at least three different positions on a surface of the biochip 20. When the 3D locations of the three different positions are calculated, a virtual approximation plane with respect to the surface of the biochip 20 is determined using, for example, a general regression analysis method, such as a least squares method, but additional example embodiments are not limited thereto. In at least one embodiment, the positions to be measured on the surface of the biochip 20 may be determined in advance.

Figure 2:
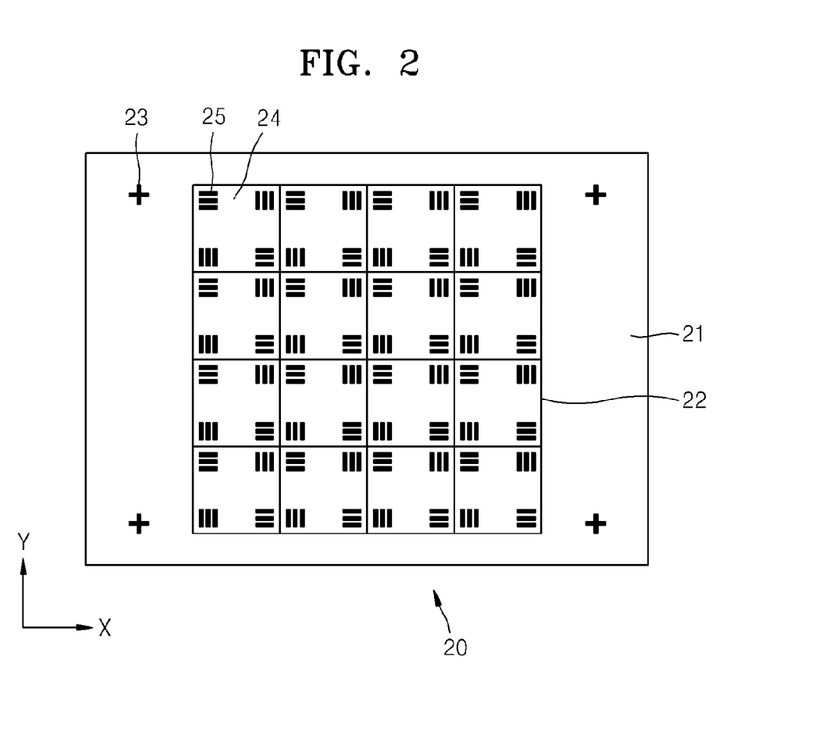
FIG. 2 is a plan view of a structure of a surface of a biochip to be scanned according to an example embodiment.

FIG. 2 is a plan view of a structure of the surface of the biochip 20 to be scanned according to an example embodiment. Referring to FIGS. 2 and 7, a microarray 22 of spots 27 (FIG. 6) is disposed on, e.g., is formed on, a substrate 21 formed of a material such as glass or silicon, nut not being limited thereto. Target marks 23 are formed on the substrate 21 outside a periphery the microarray 22, for example, as shown in FIG. 2. The target marks 23 may be, for example, predetermined patterns formed of metal, but additional example embodiments are not limited thereto. The target marks 23 are shown as having a plus- or cross-shape in FIG. 2 but, alternatively, may be formed as patterns having a different shape. In addition, while four target marks 23 are illustrated in FIG. 2, a number of target marks 23 may be different than four. In one example embodiment, at least three target marks 23 may exist to obtain the virtual approximation plane with respect to the surface of the biochip 20. If four or more target marks 23 exist, a virtual approximation curved surface with respect to the surface of the biochip 20 may also be obtained. In still additional example embodiments, one or more target marks 23 may be disposed in the microarray 22 of spots.

A pattern shape of the target marks 23 disposed on the substrate 21 may be stored in advance in a memory (not shown) of the computer 13, for example. Thus under control of the computer 13, the camera 12 moves in the X and Y directions to search for the target marks 23. When the target marks 23 are found, the camera 12 may move in the Z direction and focus on the target marks 23. Then, the 3D locations of the target marks 23 are calculated based on degrees of motion of the stage 11 required until the camera 12 focuses on the target marks 23. As a result, the 3D locations are sequentially calculated with respect to the at least three target marks 23. The measured 3D locations of the target marks 23 are inputted to the computer 13. Thus, in operation S2 (FIG. 7), the computer 13 calculates the virtual approximation plane with respect to the surface of the biochip 20 by using the input 3D locations of the target marks 23. In one or more embodiment, as described above, a general regression analysis method such as a least squares method, for example, may be used. In addition, when the 3D locations of four or more target marks 23 are determined by the computer 13, the virtual approximation curved surface with respect to the surface of the biochip 20 may also be calculated in operation S2.

When the virtual approximation plane or the curved surface with respect to the surface of the biochip 20 is determined (operation S2), degrees of rotation and tilt of the biochip 20, with respect to the moving axis of the camera 12, may be determined in operation S3. After the degrees of rotation and tilt of the biochip 20 are determined, imaging locations of the panels 24 and, more particularly, panels 24 that are continuous, e.g., adjacent to each other, on the biochip 20 are determined (operation S4), and, accordingly, the biochip 20 may be scanned (in operation S5).

Referring again to FIG. 2, the microarray 22 of spots 27 (FIG. 6) are disposed on a plurality of panels 24, and the panels 24 are used as basic units of imaging. Although only sixteen panels 24 are illustrated in FIG. 2, a number of the panels 24 may be different from, e.g., less than or greater than, sixteen in additional example embodiments. The panels 24 may be separated from each other in advance and, additionally, panel marks 25 are formed on each of the panels 24 to identify and differentiate regions of the panels 24 from each other. For example, the panel marks 25 may be formed at four corners of each of the panels 24, but oriented differently in adjacent panels 24, as shown in FIG. 2. Thus, the panels 24 in the microarray 22 of spots may be identified based on the panel marks 25.

Figure 3:
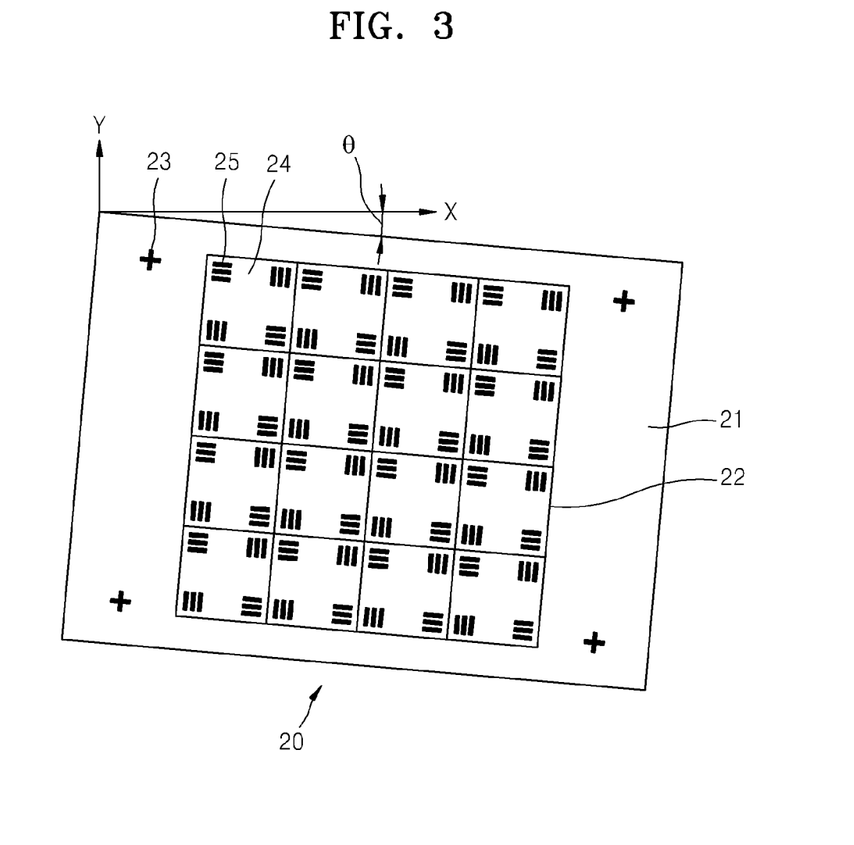
FIG. 3 is a plan view a biochip that is rotated with respect to a moving axis of a camera according to an example embodiment.

The imaging locations of the panels 24 on the biochip 20 are determined with respect to the degrees of rotation and tilt of the biochip 20. Hereinafter, a method of determining the imaging locations when the biochip 20 is rotated with respect to the moving axis of the camera 12 will be described in further detail with reference to FIGS. 3-7. FIG. 3 is a plan view of the biochip 20 rotated by a rotation angle $\theta$ with respect to the moving axis of the camera 12, according to an example embodiment. When an image of a single panel 24 is obtained, an imaging range of the camera 12 is controlled to cover from about 10 percent (%) to about 15% of an area outside a periphery of the single panel 24. Thus, the imaging range of the camera 12 is greater than the size of a single panel 24 by about 10% to about −15%. Thus, when the rotation angle $\theta$ of the biochip 20 is small (such as when a deviation in the Y direction between the panels 24 in first and last columns in the X direction is within about 10% to about 15% for example,), the rotation angle $\theta$ may not need to be compensated for. Specifically, for example, when a row of the panels 24 along the X direction is being scanned, the camera 12 may move only in the X direction (without moving in the Y direction) to scan the panels 24. In this case, after X and Y coordinates of a center portion of a panel 24, which is initially scanned, are determined with reference to the panel marks 25 of the panel 24, the X and Y coordinates of center portions of the other panels 24, which are subsequently scanned, are sequentially determined based on predetermined widths and lengths of the panels 24. In addition, the panels 24 in the same row have the same Y coordinate, while the panels 24 in the same column have the same X coordinate.

Figure 4:
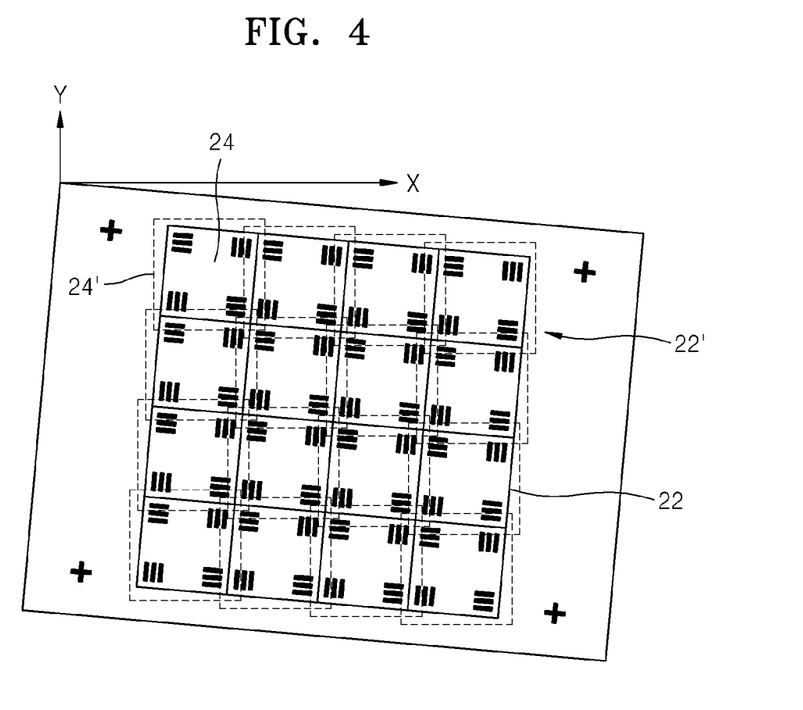
FIG. 4 is a plan view that illustrates an arrangement of virtual panels of a biochip to be scanned by a camera of a scanner device when the biochip is rotated, according to an example embodiment.

When the rotation angle $\theta$ of the biochip 20 is large, however, the rotation angle $\theta$ is compensated for. Thus, when a row of the panels 24 along the X direction are being scanned, for example, the camera 12 moves in the Y direction, as well as in the X direction. Also, when a subsequent row of the panels 24 is scanned, a coordinate in the X direction is modified by a value corresponding to the rotation angle $\theta$. In this case, when the row of the panels 24 in the X direction is being scanned, a modification in the Y direction is set to correspond to the rotation angle θ. Likewise, when a subsequent row of the panels 24 is scanned, a modification in the X direction is also set to correspond to the rotation angle θ. When the X and Y coordinates of a center portion of the panel 24, which is initially scanned, are determined with reference to the panel marks 25 of the panel 24, the computer 13 sequentially determines the X and Y coordinates of center portions of the other panels 24, which are subsequently scanned, based on the widths and lengths of the panels 24 and the rotation angle θ of the biochip 20. Specifically, as shown in FIG. 4, which is a plan view of an arrangement of virtual panels 24' of the biochip 20 to be scanned by the camera 12 when the biochip 20 is rotated, the camera 12 scans each virtual panels 24' by taking into consideration a virtual microarray 22' of spots disposed in a stair-shaped pattern corresponding to the rotation angle θ. In addition, the virtual panels 24' are arranged in a shape of partially overlapped stairs having the virtual microarray 22' of spots 27 (FIG. 6), as shown in FIG. 4.

Figure 5:
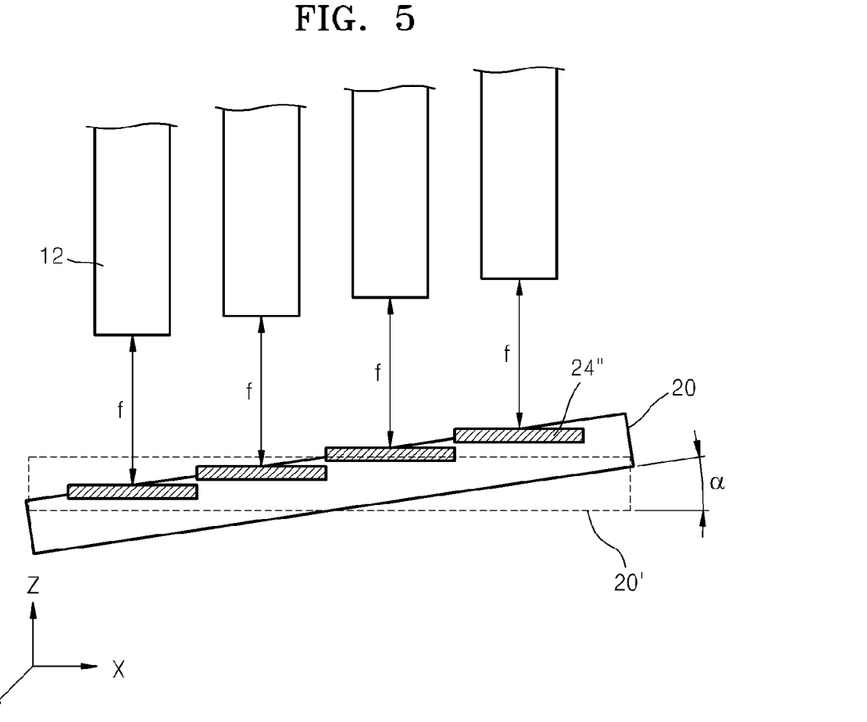
FIG. 5 is a partial cross-sectional view of virtual panels of a biochip to be scanned by a camera of a scanner device when the biochip is tilted, according to an example embodiment.

Referring now to FIG. 5, which is a partial cross-sectional view of an arrangement of virtual panels 24" of the biochip 20 to be scanned by the camera 12 when the biochip 20 is tilted, a dotted portion, which represents an ideal biochip 20', e.g. a biochip 20 that is horizontally disposed without being tilted, is shown. The biochip 20, however, is actually tilted from the ideal biochip 20' location by a tilt angle α, as shown in FIG. 5. Thus, when the camera 12 moves only in a horizontal direction, e.g., in the X direction (as viewed in FIG. 5), a distance between the camera 12 and the biochip 20 changes, and the camera 12 goes out of focus. As a result, imaging locations of each of the panels 24 along the X direction are separately determined to maintain a fixed distance, which corresponds to a focal length f, measured along the Z direction, of the camera 12 between the camera 12 and the biochip 20.

More specifically, for example, when the camera 12 moves in the X direction (and/or in the Y direction), the camera 12 also gradually moves in the Z direction to maintain the fixed focal distance f between the camera 12 and the biochip 20, as shown in FIG. 5. In this case, when the camera 12 is moving in the X direction, for example, an adjustment of the camera 12 in the Z direction is set to correspond to the tilt angle α. To adjust the camera 12, after a z coordinate of the center portion of the panel 24, which is initially scanned, is determined with reference to the panel marks 25 of the panel 24, the computer 13 sequentially determines Z coordinates of center portions of the other panels 24, which are subsequently scanned, based on the widths and lengths of the panels 24 and the tilt angle α of the biochip 20. Virtual panels 24", calculated as described above, are illustrated in FIG. 5. The camera 12 scans each of the virtual panels 24" by assuming that the horizontally arranged virtual panels 24" are arranged in a stair shape in the Z direction, as shown in FIG. 5.

Although a particular tilt angle α commonly applied with respect to both the X and Y directions is illustrated in FIG. 5 for purposes explanation, it will be noted that additional example embodiments are not limited thereto. Specifically, for example, a tilt angle of the biochip 20 in the X direction may differ from a tilt angle of the biochip 20 in the Y direction. Thus, an increment in the Z direction when the camera 12 moves in the X direction and an increment in the Z direction when the camera 12 moves in the Y direction may be independently calculated based on the two tilt angles with respect to the X and Y directions. Specifically, the two increments may be calculated based on the virtual approximation plane or curved surface with respect to the surface of the biochip 20 discussed in greater detail above. As a result, 3D coordinates (e.g., X, Y, Z coordinates) of center portions of all of the panels 24 on the virtual approximation plane or curved surface with respect to the surface of the biochip 20 may be determined and, thus, imaging locations of all of the panels 24 may be determined to properly maintain the focal length f of the camera 12 from the biochip 20.

As described in greater detail above, and referring again to FIGS. 1 and 7, the computer 13 controls a scanning operation of the camera 12 based on the determined imaging locations of the panels 24. Thus, under the control of the computer 13, the camera 12 obtains images of each of the panels 24 on the biochip 20 by scanning the biochip 20 (operation S5). In a conventional method, a camera obtains an image of a single panel, and then a new focusing operation must be performed each time the camera moves to a subsequent/adjacent panel, to obtain an image of the subsequent/adjacent panel. Thus, in a conventional device, a number of times a focusing operation is required to be performed corresponds to the number of panels. However, according to the example embodiments described herein, such as in the method illustrated in FIG. 7, the computer 13 calculates optimal imaging locations of the camera 12 in advance and, as a result, a focusing operation is not performed for each of the panels 24 while the panels 24 are being scanned. Instead, the focusing operation is performed only once, e.g., when the 3D locations of the target marks 23 are being calculated in an initial operation. Thus, the number of times the focusing operation is required to be performed corresponds to the number of target marks 23. Thus, a scanning time of the biochip 20 is substantially reduced.

As the panels 24 on the biochip 20 are scanned, an image of each of the panels 24 is stored in the memory (not shown) of the computer 13. Accordingly, in operation S6 (FIG. 7), image processing software, for example, installed in the computer 13 performs a gridding operation on the obtained images of the individual panels 24. More specifically and referring now to FIG. 6, which is a plan view of an image 30 of a single panel 24, obtained by the camera 12 of the biochip scanner device 10, on the image 30, the single panel 24 is located in the middle and adjacent panels 24 are disposed around a periphery of single the panel 24. Also, a plurality of spots 27 is disposed on the panel 24, and the panel marks 25 are located at corners of the panel 24, as described in greater detail above. Although not shown in FIG. 6, a brightness of the spots 27 may vary according to a number of genes in a sample, for example, which is combined with each of the spots 27. The gridding operation of operation S6 includes coordinating locations of the spots 27 on the imaged panel 24 and evaluating the brightness of each of the spots 27.

The image processing software removes unneeded images from one or more of the adjacent panels 24, based on the panel marks 25. The image processing software coordinates locations of individual spots 27 on the panel 24 into X and Y coordinates (with reference to the panel marks 25), and extracts data regarding the brightness of each of the spots 27 for each coordinate. In this case, the degrees of rotation and tilt of the biochip 20, which are determined in operation S3, may be considered. Specifically, for example, to compensate for the degree of rotation of the biochip 20 before extracting the data, the image processing software may rotate the image 30 by the degree of rotation (e.g., by the rotation angle θ) of the biochip 20, which is determined in operation S3. Also, although the panel 24 is scanned in units of horizontally-aligned virtual panels 24" (FIG. 5), some spots 27 are farther from the camera 12 than other spots 27, while and some spots 27 are closer to the camera 12 than other spots 27, since the panel 24 is actually tilted. The image processing software compensates an actual brightness of the spots 27 on the image 30 with reference to a tilt direction and degree of tilt (e.g., the tilt angle α) of the biochip 20, which is calculated in operation S3.

As a result, the gridding operation of operation S6, which is performed on the image 30 of an individual panel 24, is performed for each of the panels 24 of the biochip 20. Then, in operation S7, data for the entire biochip 20 is extracted from gridding results of the image 30 for every individual panel 24. More particularly, locations of all of the spots 27 on the microarray 22 of the biochip are coordinated, and the brightness of each spot 27 is evaluated by combining data of each of the individual panels 24. In an example embodiment, this is performed by adding a coordinate of each panel 24 to coordinates of the spots 27 on the panel 24.

A method of extracting the data of the entire biochip 20 from the gridding results of the image 30 of every individual panel 24, as performed in operation S7 (FIG. 7), will now be described in further detail with reference to FIGS. 1 and 7. Whenever the camera 12 scans a given panel 24 on the biochip 20, the computer 13 stores an image of the given panel 24 and a relative coordinate of the scanned given panel 24 with respect to the other panels 24, in the memory (not shown) of the computer 13. Specifically, for example, and referring to FIG. 2, a relative coordinate of a panel 24 located at a top-left corner to be initially scanned may be designated (0, 0). The relative coordinate of a panel 24 located at a bottom-right corner, to be scanned last, is therefore (3, 3). Accordingly, when the camera 12 obtains an image of a particular panel 24, e.g., the given panel 24, in operation S5, the computer 13 calculates the coordinate of the given panel 24.

Then, as described in greater detail above, when the gridding operation of operation S6 is performed, the image processing software converts relative locations of the spots 27 on each of the panels 24 into the x and y coordinates. Then, in operation S7, the image processing software converts the relative locations of all of the spots 27 on the biochip into the x and y coordinates with reference to the coordinate of each of the panels 24, described above. To convert the relative locations of the spots 27, the number n of spots 27 along the X direction and the number m of spots 27 along the Y direction on each of the panels 24 may be stored in the memory of the computer 13 in advance. Thus, when the spots 27 are arranged in a rectangular shape, for example, on each of the panels 24, and all of the panels 24 have the same spot arrangement thereon, a relative location of a spot 27 having a coordinate (x, y) on a panel 24 having a coordinate (X, Y) may be simply calculated as (x+n*X, y+m*Y).

In another example embodiment, rows and columns of each panel 24 may have different numbers of spots 27 for each of the panels 24, which may also have different spot arrangements thereon. In this case, when the number of spots 27 arranged in each of the rows and columns of the panel 24 is known in advance, the relative locations of all of the spots 27 on the biochip 20 may be accurately calculated according to the above-described operation. Also, the number of spots 27 arranged in each of the rows and columns of the panel 24 may be stored in the memory of the computer 13 in advance, and may be directly calculated by the image processing software in the gridding operation of the image 30 of every individual panel 24 (operation S6).

As such, when the coordinates of the spots 27 on all of the individual panels 24 are converted into coordinates with respect to the entire biochip 20 (in operation S6), calculated brightness data of the spots 27 on the individual panels 24 are matched with the converted coordinates, and the data of the spots 27 of the entire biochip 20 is thereby extracted.

As described herein, according to one or more of example embodiments of the general inventive concept, a gridding operation is individually performed on panels, and overall data is obtained from results of the gridding operation, and, as a result, an inconvenience is effectively prevented when complete panel images are individually formed and then the panel images are attached to each other without any disconnection to form a single large biochip image.

The general inventive concept should not be construed as being limited to the example embodiments set forth herein. Rather, these example embodiments are provided so that this disclosure will be thorough and complete and will fully convey the general inventive concept to those skilled in the art.

Thus, while the general inventive concept has been particularly shown and described with reference to example embodiments thereof, it will be understood by those of ordinary skill in the art that various changes in form and details may be made therein without departing from the spirit or scope of the general inventive concept as defined by the following claims.

What is claimed is:

1. A method of scanning a biochip, the method comprising:
measuring three-dimensional locations of at least three different positions on a surface of the biochip, wherein the biochip comprises two or more panels and each panel comprises a microarray, wherein the two or more panels are adjacent to each other and the at least three different positions comprise target marks on the surface of the biochip, wherein measuring includes focusing a camera on the target marks, wherein the measured three-dimensional locations of the target marks are calculated based on a degree of motion of a stage on which the biochip is disposed;
determining one of a virtual approximation plane and a curved surface with respect to the surface of the biochip based on the measured three-dimensional locations;
determining a degree of rotation of the biochip relative to a scanning direction and imaging locations of the two or more panels disposed on the biochip based on the one of the virtual approximation plane and the curved surface;
obtaining individual images of the two or more panels by scanning the biochip based on the determined imaging locations, wherein scanning includes adjusting a position of one of the camera or the biochip in the scanning direction and in a first direction orthogonal to the scanning direction during the scanning in the scanning direction and, if the degree of rotation is larger than a predetermined angle, in a second direction orthogonal to the scanning direction during the scanning in the scanning direction, wherein the first direction and the second direction are orthogonal; and
extracting overall data of the biochip from the individual images of the two or more panels,
wherein the extracting of the overall data of the biochip comprises:
performing a gridding operation on an individual image of one of the panels so as to coordinate locations of spots of a microarray in an individual panel and to evaluate a brightness of each of the spots;
sequentially performing the gridding operation on individual images of the other panels; and
extracting data of the entire biochip from results of the gridding operation performed on the individual images of the panels.

2. The method of claim 1 wherein the target marks are disposed outside a microarray of spots disposed on the substrate.

3. The method of claim 1, wherein the one of the virtual approximation plane and the curved surface is determined by using a least squares method based on the measured three-dimensional locations.

4. The method of claim 1, wherein the determining the imaging locations comprises:
   determining a degree of tilt of the biochip based on the one of the virtual approximation plane and the curved surface;
   determining x and y coordinates of center portions of the two or more panels based on the determined degree of rotation of the biochip;
   determining z coordinates of the center portions of the two or more panels based on the determined degree of tilt of the biochip; and
   calculating three-dimensional coordinates of the imaging locations based on a focal length of a camera and the x, y and z coordinates of the center portions of the two or more panels.

5. The method of claim 4, wherein the determining the x and y coordinates comprises:
   determining x and y coordinates of a center portion of an initially scanned panel of the two or more panels; and
   determining x and y coordinates of center portions of subsequently scanned panels of the two or more panels, based on widths and lengths of each of the two or more panels and the determined degree of rotation of the biochip.

6. The method of claim 4, wherein the determining the z coordinates comprises:
   determining a z coordinate of a center portion of an initially scanned panel of the two or more panels; and
   determining z coordinates of center portions of subsequently scanned panels of the two or more panels, based on widths and lengths of each of the two or more panels and the determined degree of tilt of the biochip.

7. The method of claim 4, wherein the obtaining the individual images of the panels comprises scanning the two or more panels by moving the camera based on the determined imaging locations.

8. The method of claim 1, wherein the performing the gridding operation on the individual images of each of the two or more panels comprises rotating the individual images by the degree of rotation of the biochip.

9. The method of claim 1, wherein the performing the gridding operation on the individual images of each of the two or more panels comprises compensating the brightnesses of the spots based on a tilt direction and the degree of tilt of the biochip.

10. The method of claim 1, wherein the extracting the data of the entire biochip comprises:
    calculating relative coordinates of single panels of the two or more panel with respect to the other panels of the two or more panels;
    converting coordinates of the spots on each of the panels of the two or more panels into coordinates referenced to the entire biochip based on coordinates of each of the panels and the coordinates of the spots on each of the panels; and
    matching brightness data of the spots on each of the panels, which is calculated by performing the gridding operation, with the converted coordinates of the spots on each of the panels.

11. The method of claim 10, wherein the converting the coordinates of the spots comprises:
    multiplying the coordinates of each of the panels by the number of spots arranged in X and Y directions on each of the panels; and
    adding a resultant value of the multiplying the coordinates to the coordinates of the spots on each of the panels.

12. The method of claim 11, wherein the number of spots arranged in the X and Y directions on each of the panels is determined based on a value stored in advance of the multiplying the coordinates of each of the panels by the number of spots.

13. The method of claim 11, wherein the number of spots arranged in the X and Y directions on each of the panels is calculated when the gridding operation is performed.

14. The method of claim 1, wherein panel marks are formed on each of the two or more panels.

15. The method of claim 14, wherein the panel marks are formed at corners of each of the two or more panels.

16. A biochip scanning apparatus comprising:
    a stage;
    a biochip disposed on the stage, wherein the biochip comprises two or more panels and each panel comprises a microarray, wherein the two or more panels are adjacent to each other;
    a camera which generates images of the biochip; and
    a computer which controls the stage and the camera, and determines data about the biochip by analyzing the images,
    wherein the computer controls the stage and the camera to:
    measure three-dimensional locations of at least three different positions on a surface of the biochip, wherein the at least three different positions comprise target marks on the surface of the biochip, wherein the measured three-dimensional locations of the target marks are calculated based on a degree of motion of the stage on which the biochip is disposed;
    determine one of a virtual approximation plane and a curved surface with respect to the surface of the biochip based on the measured three-dimensional locations;
    determine a degree of rotation of the biochip relative to a scanning direction and imaging locations of the two or more panels disposed on the biochip based on the one of the virtual approximation plane and the curved surface;
    obtain individual images of the two or more panels by scanning the biochip based on the determined imaging locations, wherein scanning includes adjusting a position of one of the camera or the biochip in the scanning direction and in a first direction orthogonal to the scanning direction during the scanning in the scanning direction and, if the degree of rotation is larger than a predetermined angle, in a second direction orthogonal to the scanning direction during the scanning in the scanning direction, wherein the first direction and the second direction are orthogonal; and
    extract overall data of the biochip from the individual images of the two or more panels by:
    performing a gridding operation on an individual image of one of the panels so as to coordinate locations of spots of a microarray in an individual panel and to evaluate a brightness of each of the spots;
    sequentially performing the gridding operation on individual images of the other panels; and
    extracting data of the entire biochip from results of the gridding operation performed on the individual images of the panels.

17. The biochip scanning apparatus of claim 16, wherein the at least three different positions comprise target marks on a substrate of the biochip, and the target marks are disposed outside a microarray of spots disposed on the substrate.

18. An apparatus for scanning a biometric device, the apparatus comprising:
a camera which generates images of the biometric device, wherein the biometric device comprises two or more panels and each panel comprises a microarray; and
a computer which extracts data from the images, wherein the apparatus:
measures three-dimensional locations of at least three different positions on a surface of the biometric device, wherein the two or more panels are adjacent to each other and the at least three different positions comprise target marks on the surface of the biometric device, wherein the measured three-dimensional locations of the target marks are calculated based on a degree of motion of a stage on which the biometric device is disposed;
determines one of a virtual approximation plane and a curved surface with respect to the surface of the biometric device based on the measured three-dimensional locations;
determines a degree of rotation of the biometric device relative to a scanning direction and imaging locations of the two or more panels disposed on the biometric device based on the one of the virtual approximation plane and the curved surface;
obtains individual images of the two or more panels by scanning the biometric device based on the determined imaging locations, wherein scanning includes adjusting a position of one of the camera or the biometric device in the scanning direction and in a first direction orthogonal to the scanning direction during the scanning in the scanning direction and, if the degree of rotation is larger than a predetermined angle, in a second direction orthogonal to the scanning direction during the scanning in the scanning direction, wherein the first direction and the second direction are orthogonal; and
extracts overall data of the biometric device from the individual images of the two or more panels by:
performing a gridding operation on an individual image of one of the panels so as to coordinate locations of spots of a microarray in an individual panel and to evaluate a brightness of each of the spots;
sequentially performing the gridding operation on individual images of the other panels; and
extracting data of the entire biometric device from results of the gridding operation performed on the individual images of the panels.

19. The apparatus of claim 18, wherein the biometric device comprises one of a deoxyribonucleic acid biochip and a protein biochip.

20. The apparatus of claim 18, wherein
the at least three different positions comprise target marks on a substrate of the biometric device,
the target marks are disposed outside a microarray of spots disposed on the substrate, and
panel marks are formed at corners of each of the two or more panels.

21. A method of scanning a biochip, the method comprising:
measuring three-dimensional locations of at least three different positions on a surface of the biochip, wherein the biochip comprises two or more panels, wherein the two or more panels are adjacent to each other and the at least three different positions comprise target marks on the surface of the biochip, wherein the measured three-dimensional locations of the target marks are calculated based on a degree of motion of a stage on which the biochip is disposed;
calculating one of a virtual approximation plane and a curved surface with respect to the surface of the biochip based on the measured three-dimensional locations;
determining a degree of rotation of the biochip relative to a scanning direction and imaging locations of the two or more panels disposed on the biochip based on the one of the virtual approximation plane and the curved surface;
obtaining individual images of the two or more panels by scanning the biochip based on the imaging locations, wherein scanning includes adjusting a position of one of a camera or the biochip in the scanning direction and in a first direction orthogonal to the scanning direction during the scanning in the scanning direction and, if the degree of rotation is larger than a predetermined angle, in a second direction orthogonal to the scanning direction during the scanning in the scanning direction, wherein the first direction and the second direction are orthogonal; and
determining data about the biochip from the individual images of the two or more panels.

* * * * *